United States Patent

Perez et al.

[11] Patent Number: 6,132,701
[45] Date of Patent: Oct. 17, 2000

[54] METHOD FOR REDUCING ORAL MALODOR

[76] Inventors: Narciso C. Perez; Virginia C. Perez, both of 16339 SR 65, Wapakoneta, Ohio 45895

[21] Appl. No.: 09/213,212

[22] Filed: Dec. 17, 1998

[51] Int. Cl.⁷ ............................ A61K 7/16; A61K 33/08
[52] U.S. Cl. ........................ 424/49; 424/688; 424/693; 424/694
[58] Field of Search ................. 424/49–58, 688, 424/693, 694

[56] References Cited

U.S. PATENT DOCUMENTS

| | | |
|---|---|---|
| 4,041,149 | 8/1977 | Gaffar et al. . |
| 4,112,066 | 9/1978 | Hussein ........................ 424/49 |
| 4,150,141 | 4/1979 | Berger . |
| 4,167,559 | 9/1979 | Michel . |
| 4,457,909 | 7/1984 | Tames . |
| 4,689,215 | 8/1987 | Ratcliff . |
| 5,286,479 | 2/1994 | Garlich et al. . |
| 5,688,492 | 11/1997 | Galley et al. . |
| 5,703,122 | 12/1997 | Duffy . |
| 5,738,840 | 4/1998 | Richter . |
| 5,747,079 | 5/1998 | Hoffman . |
| 5,753,217 | 5/1998 | Christopfel . |

OTHER PUBLICATIONS

Moeller, et al., "Metals and Metallurgy", Chemistry, 1989, p. 671, Harcourt, Brace, Jovanovich (pub.), New York, USA.
"Lime Lighting—Maximillian", Encyclopedia Britannica, 1965c, p. 34–35, vol. 14, William Benton (pub.).
"Calcium Botha—Carthage", Encyclopedia Britannica, 1965c, p. 594–596, vol. 4, William Benton (pub.).

*Primary Examiner*—Shep K. Rose
*Attorney, Agent, or Firm*—Dale J. Ream

[57] ABSTRACT

A method for reducing oral malodor associated with halitosis includes containing the oral cavity of a person with an aqueous solution containing calcium hydroxide. The method includes the steps of mixing approximately one-half ounce of pure lime with every two gallons of water which causes an exothermic chemical reaction to form calcium hydroxide. The calcium hydroxide is slightly soluble in water and is thus allowed to settle to the bottom of the container, leaving an aqueous solution having a predetermined proportion of dissolved and suspended calcium hydroxide. This solution is withdrawn from the container for ingestion or for oral cavity rinse by a person.

11 Claims, 1 Drawing Sheet

METHOD FOR REDUCING ORAL MALODOR

BACKGROUND OF THE INVENTION

The present invention generally relates to methods and compositions for the treatment or prevention of mouth odors and, more particularly, to a method of using a calcium hydroxide solution to reduce or eliminate oral malodor related to halitosis.

Halitosis, better known as oral malodor or bad breath, is a socially undesirable condition caused by anaerobic bacteria which accumulates at the back of the tongue. The bacteria generate malodorous volatile sulfur compounds which are then expelled from the mouth through normal breathing.

Various methods and compositions have been proposed in the prior art for managing, reducing, or eliminating halitosis. Some compositions propose the use of chlorine dioxide, the disadvantages of which are discussed in U.S. Pat. No. 5,747,079 to Hoffman. Other methods require multiple chemicals or expensive industrial processes.

It is desirable to have a method for ameliorating oral malodor that is simple and can be accomplished either industrially or by an individual. It is further desirable to have a method for reducing oral malodor that utilizes inexpensive and readily available substances.

SUMMARY OF THE INVENTION

A preferred embodiment of the method according to the present invention includes the steps of mixing one-half ounce of pure lime with every two gallons of water to form calcium hydroxide, an acid neutralizer, through an exothermic reaction therebetween. Alternatively, previously prepared calcium hydroxide can be deposited into the water. The calcium hydroxide is relatively insoluble in water and is thus allowed to substantially settle to the bottom of the container, leaving an aqueous solution having predetermined portions of dissolved and suspended calcium hydroxide. A portion of the solution is then withdrawn from the container and ingested or used as an oral cavity rinse by a person.

It is therefore a general object of the invention to provide a method for reducing oral malodor that is simple and inexpensive.

Another object of the invention is to provide a method for reducing oral malodor which utilizes an aqueous solution of calcium hydroxide.

A further object of the invention is to provide a method for reducing oral malodor which includes mixing a small amount of lime with water.

A still further object of the invention is to provide a method for reducing oral malodor which includes ingesting the aqueous solution of calcium hydroxide.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
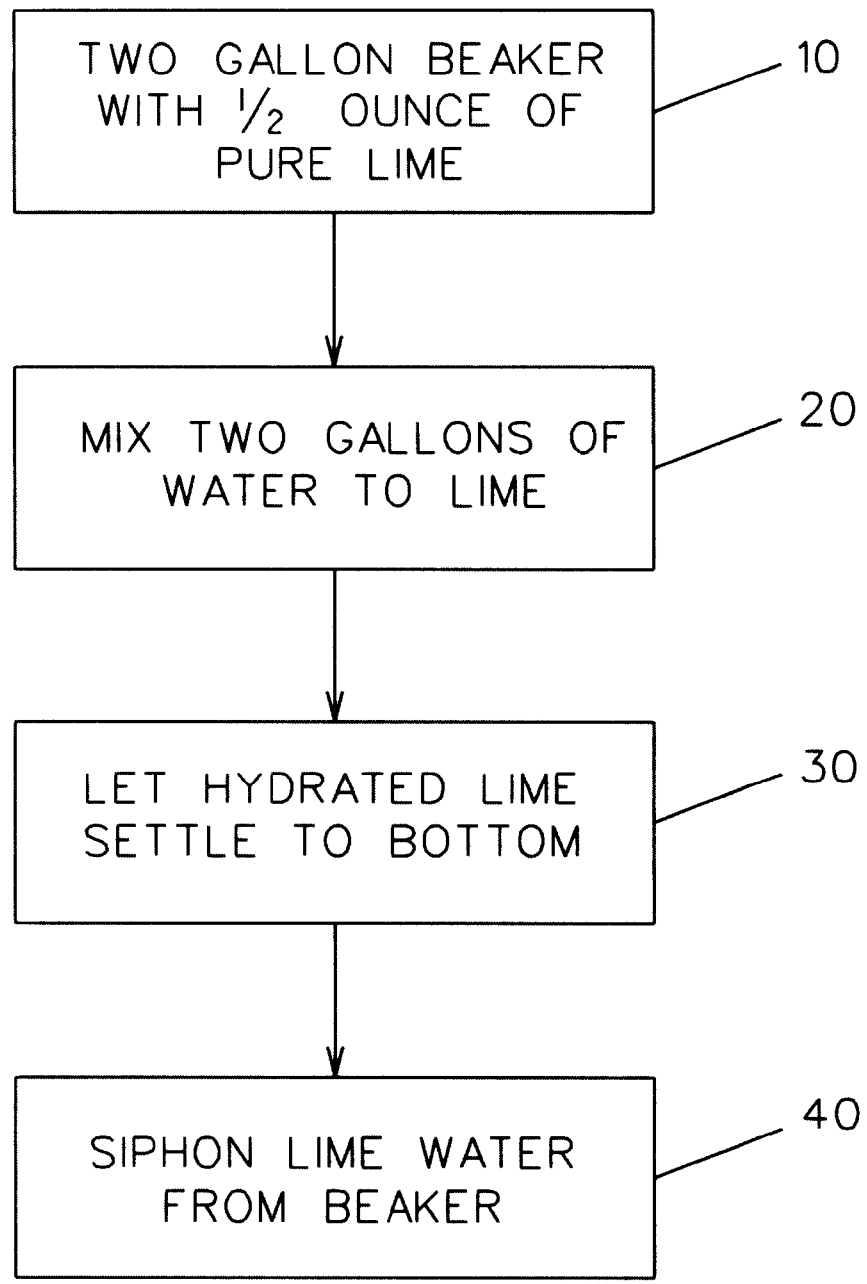
FIG. 1 is a block diagram in accordance with the preferred embodiment of the present invention showing the steps of the method.

The preferred method for reducing oral malodor in a person according to the present invention includes the steps as illustrated in FIG. 1. Although the method generally provides for reducing oral malodor through ingestion of an aqueous solution containing calcium hydroxide, the method is equally effective when the solution is used as an oral rinse.

Calcium hydroxide [$Ca(OH)_2$], also known as hydrated lime or limewater, is an alkaline solution having acid neutralization properties. Calcium hydroxide is formed through an exothermic reaction caused by mixing pure lime with water. Pure lime as well as calcium hydroxide are inexpensive and widely available substances. Calcium hydroxide, when used according to the method of the present invention, is effective to neutralize the malodorous acids found in the oral cavity and thus to reduce or eliminate halitosis.

According to the present method, pure lime is mixed with water in a ratio of one-half ounce of pure lime for every two gallons of water in a container as indicated in blocks 10 and 20 of FIG. 1. Deposition of lime into the water immediately initiates an exothermic chemical reaction in which hydrogen ions from water molecules are bonded to the pure lime molecules to form an aqueous solution of calcium hydroxide, also known as hydrated lime, according to the formula: $CaO + H_2O \rightarrow Ca(OH)_2$.

Calcium hydroxide is only slightly soluble in water. Accordingly, the insoluble portion of the calcium hydroxide is allowed to settle to the bottom of the container as indicated by block 30 for removal or reuse as further described below. The calcium hydroxide is allowed to settle for 30 minutes which allows substantially all of the calcium hydroxide to dissolve in the solution, remain suspended therein, or settle to the bottom of the container.

The aqueous solution containing dissolved or suspended calcium hydroxide is withdrawn from the container, preferably through a siphoning process so as not to include settled calcium hydroxide in the withdrawn solution 40. A portion of the solution most closely adjacent the settled hydrated lime should not be withdrawn as the concentration thereof would be too potent. The withdrawn aqueous solution is suitable for application to the oral cavity and can be immediately applied thereto or bottled for mass distribution. It is understood that a known food coloring agent may be added to the aqueous solution prior to bottling to thereby alert consumers regarding the medicinal nature of the solution.

The preferred method of applying the calcium hydroxide solution to a person's oral cavity is through ingestion. Ingesting a teaspoon of the solution daily has been found to reduce or eliminate halitosis as well as other body odor. If ingestion of the solution is undesirable, a teaspoon of the solution may be used to rinse a person's oral cavity and then be expelled therefrom.

An alternative method for preparing an aqueous solution of calcium hydroxide involves depositing previously prepared calcium hydroxide into a container of water in the same proportions previously described and allowing the calcium hydroxide to settle. Thus, proper proportions of the hydrated lime will dissolve or be suspended in the water to form the desired solution. It is understood, however, that previously used calcium hydroxide can only be used effectively approximately two times. Obviously, this limited reusability of calcium hydroxide contributes to the overall inexpensive preparation process. The remainder of the method is as previously described.

It is understood that while certain forms of this invention have been illustrated and described, it is not limited thereto except insofar as such limitations are included in the following claims and allowable functional equivalents thereof.

What is claimed is:

1. A method for reducing oral malodor associated with the condition of halitosis, comprising the steps of:
   mixing in a container one-half ounce of pure lime with every two gallons of water;
   allowing the pure lime to exothermically react with the water to form an aqueous solution of calcium hydroxide;
   allowing a predetermined amount of the calcium hydroxide to settle to the bottom of the container whereby a predetermined proportion of the calcium hydroxide remains suspended in the aqueous solution;
   withdrawing an amount of the aqueous solution containing the suspended calcium hydroxide; and
   contacting a person's oral cavity with the withdrawn aqueous solution.

2. The method as in claim 1 including the step of contacting the oral cavity daily with one teaspoon of the withdrawn aqueous solution.

3. The method as in claim 2 further including the step of ingesting the withdrawn aqueous solution.

4. The method as in claim 1 including the step of adding a coloring substance to the aqueous solution.

5. The method as in claim 1 wherein the suspended calcium hydroxide is dissolved in the aqueous solution.

6. A method for reducing oral malodor associated with the condition of halitosis comprising the steps of:
   depositing a quantity of calcium hydroxide into a container of water to form an aqueous solution;
   allowing an amount of the calcium hydroxide to settle to the bottom of the container whereby a predetermined proportion of the calcium hydroxide remains suspended in the aqueous solution;
   withdrawing an amount of the aqueous solution of suspended calcium hydroxide from the container; and
   contacting the oral cavity of a person with the withdrawn aqueous solution.

7. The method as in claim 6 including the step of contacting the oral cavity daily with one teaspoon of the withdrawn aqueous solution.

8. The method as in claim 7 further including the step of ingesting the withdrawn aqueous solution.

9. The method as in claim 7 wherein the oral malodor is reduced.

10. The method as in claim 6 including the step of adding a coloring substance to the aqueous solution whereby to alert users to the medicinal nature of the solution.

11. The method as in claim 6 wherein the suspended calcium hydroxide is dissolved in the aqueous solution.

* * * * *